United States Patent [19]

De Clercq et al.

[11] Patent Number: 5,607,922
[45] Date of Patent: Mar. 4, 1997

[54] 1,5-ANHYDROHEXITOL NUCLEOSIDE ANALOGUES

[75] Inventors: Erik D. A. De Clercq, Lovenjoel; Piet A. M. Herdewijn, Rotselaar; Arthur A. E. Van Aerschot, Heist o/d Berg, all of Belgium

[73] Assignee: Stichting Rega VZW, Belgium

[21] Appl. No.: 170,117

[22] Filed: Dec. 17, 1993

Related U.S. Application Data

[63] Continuation-in-part of PCT/BE93/00036, Jun. 18, 1993.

[30] Foreign Application Priority Data

Jun. 18, 1992 [EP] European Pat. Off. ............ 92201803.1

[51] Int. Cl.$^6$ .......................... A61K 31/70; C07H 19/06; C07H 19/16
[52] U.S. Cl. .......................... 514/43; 536/28.2; 536/27.14
[58] Field of Search .................. 514/44, 43; 536/27.1, 536/27.14, 28.2

[56] References Cited

FOREIGN PATENT DOCUMENTS

| 0217580 | 4/1987 | European Pat. Off. . |
|---|---|---|
| 0409227 | 1/1991 | European Pat. Off. . |
| 9001036 | 2/1990 | WIPO . |

OTHER PUBLICATIONS

L. Dee Nord et al., *Synthesis, Structure, and Biological Activity of Certain 2–Deoxy–β–D–ribo–hexopyranosyl Nucleosides and Nucleotides*, Journal of Medicinal Chemistry, vol. 30, No. 6 (1987), pp. 1044–1054.

Poul Hansen et al., *Synthesis of 3'–Azido–2', 3'–dideoxy–β–D–arabino–hexopyranosyl Nucleosides* Liebigs Annalen der Chemie, vol. 1990, No. 11 (1990) pp. 1079–1082.

Verheggen et al. J. Med. Chem. 36:2033–2040, 1993.

*Primary Examiner*—Gary L. Kunz
*Attorney, Agent, or Firm*—Webb Ziesenheim Bruening Logsdon Orkin & Hanson, P.C.

[57] ABSTRACT

1,5-Anhydrohexitol nucleoside analogues represented by the general formula I:

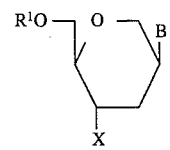

wherein the hexitol has the D-configuration and the carbon atom on which the base moiety and the X substituent stand both have the (S)-configuration and further wherein:

B is a heterocyclic ring selected from the group consisting of pyrimidine and purine bases; and X is hydrogen, azido, F, Cl, Br, I, amino, —NHR$^2$, —N(R$^2$)$_2$, —OR$^2$, —SR$^2$, or CN; wherein R$^1$ and R$^2$ are the same or different and are selected from the group consisting of hydrogen, substituted or unsubstituted C$_1$–C$_{20}$alkyl, substituted or unsubstituted C$_1$–C$_{20}$alkenyl, aroyl, C$_1$–C$_{20}$alkanoyl, and phosphoryl.

These nucleoside analogues are useful as antiviral agents against herpes simplex virus, vaccina virus, or varicella zoster virus. The definition of the X group should include —N(R$^2$)$_2$ instead of —N(N$^2$)$_2$.

14 Claims, No Drawings

1,5-ANHYDROHEXITOL NUCLEOSIDE ANALOGUES

This application is a continuation-in-part of International Patent Application No. PCT/BE93/00036 filed 18th June 1993 and designating inter alia the U.S.A.

TECHNICAL FIELD

This invention relates to nucleoside analogues with an aglycone six-membered ring which exhibits remarkable antiviral activities. This invention further relates to the chemical synthesis and the pharmaceutical and/or medical use of such nucleoside analogues.

BACKGROUND

Pentofuranosyl nucleosides are nucleosides in which a pentofuranose ring, that is, a heterocyclic five-membered ring, which is derived from pentose sugars, is bonded to the heterocyclic ring of a pyrimidine or purine base. Substituents can be present on each of both rings. Ring atoms as well as pendant hydroxy and amino groups can be replaced by other atoms or groups whereby a large number of possible variations is created.

Different pentofuranosyl nucleosides are known for their anti-viral activities. Nucleosides for example with a 2-deoxy-2-fluor-D-arabinofuranose moiety have a potential anti-viral activity against herpes viruses and are among the most active anti-herpes agents. Compare De Clercq et al., Biochem. Pharmacol. 33, 2159 (1984). A number of these nucleosides has already been tested in vivo. Their antiviral activity is dependent on the presence of a virus-specific thymidine kinase, whereby they are converted into the corresponding 5'-monophosphate derivatives. The monophosphates are further phosphorylated by cellular enzymes to triphosphates which then inhibit the viral DNA polymerase.

In the same manner base modifications of the natural 2'-deoxy nucleosides can provide these nucleotides with an anti-viral activity against herpes viruses. This activity of for instance 5-iodo-2'-deoxyuridine and E-5-(2-bromo vinyl)-2'-deoxyuridine is likewise dependent on a virus-specific thymidine kinase. Compare De Clercq et al., in Developments in Anti-viral Chemotherapy, pages 21–42 (1980), Ed. Collier and Oxford, Acad. Press.

DESCRIPTION OF THE INVENTION

The present invention relates to 1,5-anhydrohexitol nucleoside analogues, wherein a 4-substituted-2,3,4-tri-deoxy-1,5-anhydrohexitol is coupled via its 2-position to the heterocyclic ring of a pyrimidine or purine base. They are represented by the formula I:

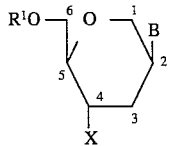

(I)

wherein B is a heterocyclic ring which is derived from a pyrimidine or purine base, and wherein X represents a hydrogen atom, azido, F, Cl, Br, I, amino —$NHR^2$, —$N(R^2)_2$, —$OR^2$, —$SR^2$ or CN, wherein $R^1$ and $R^2$ are the same or different and represent hydrogen, alkyl, acyl or phosphate groups; wherein alkyl is a straight or branched chain, saturated or unsaturated, substituted or non-substituted hydrocarbon radical with 1–20 carbon atoms; and acyl is an alkanoyl or aroyl group, wherein alkanoyl is an alkylcarbonyl radical and wherein alkyl is as described above and aroyl is a benzoyl, substituted benzoyl or naphtoyl;

or wherein X is hydrogen and a double bond is situated between the 3- and 4-position of the 1,5-anhydrohexitol ring.

Pharmaceutically acceptable salts and esters of the compound of formula I are included in the invention.

The nucleoside analogues of formula I are new compounds. They display a certain similarity with 2'-deoxypentofuranosyl nucleosides of formula II wherein B, $R^1$ and X have the same designation as in formula I, except for the enlargement of the ring with a methylene group between the ring oxide and the carbon which is coupled to the base.

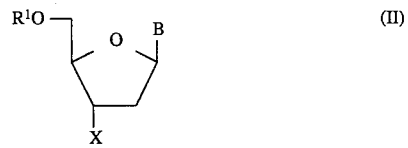

(II)

According to the invention it has been found that the nucleoside analogues of formula I and their salts and esters exhibit remarkable anti-viral properties against herpes viruses, pox viruses and related viruses. Different analogues are selectively inhibiting for Herpes simplex virus type 1, Herpes simplex virus type 2, Varicella zoster virus and Cytomegalo virus. A new class of anti-herpes agents has therefore been found.

A number of nucleoside analogues has already been described by ourselves and others, which analogues contain a pyranose group (as well as pentoses and hexoses), but not a single one has been described as possessing anti-viral activities. Compare Herdewijn et al., Nucleosides, Nucleotides 10, 119–127 (1991) (pentoses, 2-deoxy-2fluoropentopyranoses, inactive); Herdewijn et al., Bull. Soc. Chim. Belg. 99 895–901 (1990) (hexoses, inactive); Kaluza et al., Acta Chem. Scand. 44 294–296 (1990) and Hansen et al., Liebigs Ann. Chem. 1079–1082 (1990) (3-azidopyranoid analogues of AZT, inactive); Nord et al., J. Med. Chem. 30, 1044–1054 (1987) (2-deoxy-hexopyranoses, from inactive to very low activity). Until now it has not been found of a single hexose nucleoside that it is a substrate for cellular or viral kinases and thereby has an anti-viral effect. Insertion of an additional oxygen or nitrogen in the pentofuranose group, whereby analogues were created with a dioxane or morpholine moiety, equally did not provide the obtained compounds with any desired anti-viral properties. Compare Van Aerschot et al., Bull. Soc. Chim. Belg. 99 769–777 (1990).

The fact that anti-viral activities are found among the nucleoside analogues of formula I must be deemed surprising despite their configurational analogy with nucleosides of formula II. The effect of enlarging the pentofuranosyl ring to a 1,5-anhydrohexitol ring could not be anticipated beforehand. This is illustrated by the absence of anti-viral properties in the above mentioned derivatives.

The invention also relates to pharmaceutical compositions from the nucleoside analogues of formula I and, where possible, to the use of these nucleoside analogues in therapy, for instance in the treatment or prophylaxis of virus infections, in particular herpes virus infections, for example Herpes Simplex Virus types 1 and 2, Cytomegalo virus and Varicella Zoster virus.

More Detailed Description of the Invention

Compounds

The invention will now be described in more detail. The compounds according to the invention are nucleoside analogues wherein a 4-substituted-2,3,4-trideoxy-1,5anhydrohexitol is coupled via its 2-position to the heterocyclic ring of a pyrimidine or purine base. They can be represented by the above stated formula I, wherein B, $R^1$ and X have the above stated designations. Pharmaceutically acceptable salts and esters are likewise included.

The hexitol has the (D)-configuration and the carbon atom on which the base and the X substituent stand have the (S)-configuration.

Group B is derived from a pyrimidine or purine base. When derived from a pyrimidine base it can be represented by formula III:

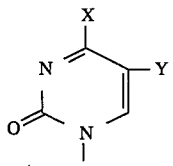

wherein X represents OH, $NH_2$ or NHQ,

Q is OH or $C_{1-5}$ alkyl,

Y is H, F, Cl, Br, I, $C_{1-5}$ alkyl, haloethyl or CH=CH—R wherein R represents halogen or $C_{1-5}$ alkyl and haloethyl with 1–4 F, Cl or Br atoms.

When B is a heterocyclic ring which is derived from a purine base it can be an adenine, guanine, 2,6-diaminopurine, hypoxanthine or xanthine ring, optionally substituted by halogen, $C_{1-5}$ alkyl or —CH=CH—R, wherein R represents hydrogen, halogen or $C_{1-5}$ alkyl.

In addition, aza, deaza, deoxy or deamino analogues of each of the said heterocyclic rings, optionally with one or more of above mentioned substituents, can be present in the compounds of formula I.

Substituents $R^1$ and X have the designation as stated above.

The compounds 1,5-anhydro-2,3-dideoxy-2-(5-iodo-uracil-1-yl)-D-arabinohexitol and 1,5-anhydro-2,3-dideoxy-2-(5-ethyl-uracil-1-yl)-D-arabinohexitol are preferred compounds of the invention having especially advantageous anti-herpes simplex (1 and 2) activity.

Chemical synthesis

The nucleoside analogues of the present invention can be prepared in different ways. In a preferred method the corresponding ($R^1$, $R^2$) substituted 1,5-anhydrohexitol ring protected in appropriate manner is first produced with a hydroxyl residue in its 2-position in the (R) configuration (formula IV).

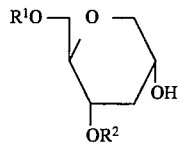

Activation with a leaving group provides nucleophile replacement with a purine or pyrimidine base, followed by deprotection of the desired nucleoside analogues (formula XIII). Substituents in 4-position (position X in formula I) can be introduced in accordance with classical and known reaction schedules which are used for introduction of substituents X in formula II (2,'-deoxypentofuranosyl nucleoside analogues)

In similar manner the preparation of the 1,5-anhydrohexitol ring can be performed in different ways. A preferred method is elucidated in the following schedule.

The synthesis begins with glucose (V) which is converted into tetra-O-acetyl-glucopyranosyl bromide (VI) in accordance with Kartha et al., J. Carbohydrate Chem. 9, 777–781 (1990).

Reduction is achieved with tri-n-butyltinhydride [which can be generated in situ from bistributyltinoxide and a polymethylhydrosiloxane, in accordance with Kocienski et al., Carbohydrate Res. 110, 330–332 (1982)], or with other reducing means which provide compound VII. Removal of the acetyl groups with sodium methoxide is followed by introduction of a benzylidene protective group, analogously of protection of methylglucoside [Methods in Carbohydrate Chemistry, vol. 2, p. 208] whereby compound VIII is obtained. Selective reaction of the hydroxyl in position 2 is feasible after previous activation with dibutyltinoxide. Position 2 can either be selectively protected, for instance as an ester (for example R =$CH_3C_6H_4CO$) or can be functionalized with a leaving group (for example R=$CH_3C_6H_4SO_2$, formula IX). The hydroxyl group in position 3 is subsequently removed [(for instance by Barton deoxygenation, see Barton et al., Tetrahedron Lett. 30, 2619–2622 (1989)] whereby the compound of formula X is obtained.

Coupling of the purine or pyrimidine base can be performed substantially in three ways:

a) by nucleophile replacement of the leaving group in position 2 with the respective purine or pyrimidine base. Compare for example Medich et al., Tetrahedron Lett. 28, 4131–4134 (1987).

b) by hydrolysis of the temporary protective group R, whereby the compound of formula X is obtained, wherein R=H, followed by alkylation of the purine or pyrimidine base under modified Mitsunobu conditions. Compare Jenny et al., Tetrahedron Lett. 32, 7029–7032 (1991).

c) by constructing the heterocyclic base by standard procedures after introduction of an amine function in the (S) configuration (formula XI). For a survey of the construction of the base for a carbocyclic amine compare Marquez and Lim, Medicinal Res. Rev. 6, 1–40 (1986).

The resulting product of formula I can be purified by standard procedures. In the alternative case a hydroxyl group in the 3-position can be removed during reduction after introduction of the base in the 2-position.

Pharmaceutically acceptable salts and esters of the nucleoside analogues of formula I can further be prepared in conventional manner.

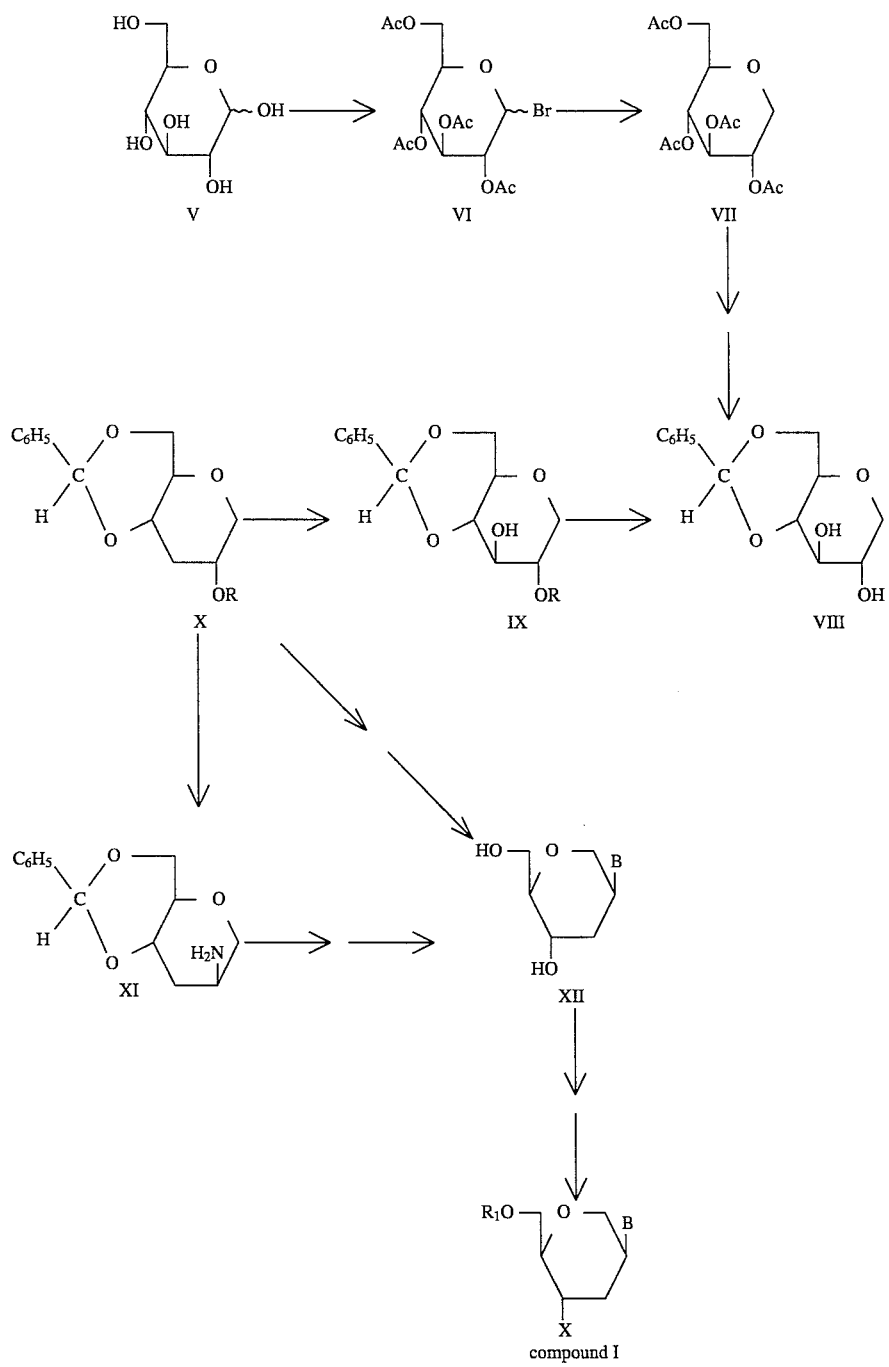

compound I

As stated above, the nucleoside analogues of the present invention generally have anti-viral activities against herpes viruses, pox viruses and related viruses, such as Herpes Simplex Virus 1, Herpes Simplex Virus type 2, Varicella zoster virus, Cytomegalo virus and vaccinia virus. In this manner they can advantageously be used for treating the diseases caused by such viruses in human and veterinary medicine.

The invention also provides:

a) compounds of formula (I) and their pharmaceutically acceptable salts and esters for use in medical therapy for example for the treatment of prophylaxis of viral-infections including those referred to above; and b) use of compounds of formula (I) and their pharmaceutically acceptable salts and esters in the manufacture of a medicament for the treatment or prophylaxis of viral-infections including those referred to above.

Pharmaceutical compositions

Pharmaceutical compositions containing the nucleoside analogues of the invention as an active ingredient can take the form of tablets, capsules, powders, suspensions, solutions, emulsions as well as salves and creams, and can be used for parenteral (intravenous, intradermal, intramuscular, intrathecal etc.) injections, oral, rectal, intravaginal and intranasal administering or for local application (for instance on skin injuries, mucosa and eyes). Such compositions can be prepared by combining the active ingredient(s) with pharmaceutically acceptable excipients normally used for this purpose. Such excipients can comprise aqueous and non-aqueous solvents, stabilizers, suspension agents, dispersing agents, moisturizers and the like, and will be known to the skilled person in the pharmaceutical field. The composition may further contain likewise suitable additives such as for instance polyethylene glycols and, if necessary, colorants, fragrances and the like.

The pharmaceutical compositions will preferably contain at least 0.1 volume % by weight of the active ingredient. The actual concentration will depend on the disease and the chosen administering route. In general this concentration will lie between 0.1 and 100% for the above applications and indications. The dose of the active ingredient to be administered can further vary between 0.1 mg and 100 mg per kg body weight, preferably between 0.1 mg and 50 mg per kg body weight, and most preferably between 0.5 mg and 20 mg per kg body weight.

The desired dose is preferably presented in the form of two, three, four, five, six or more sub-doses which are administered at appropriate intervals per day. These sub-doses can be administered in the form of dosage units containing for instance from 1 to 1500 mg, preferably from 5 to 1000 mg and most preferably from 10 to 700 mg active constituent per dosage unit, and if the condition of the patient requires the dose can, by way of alternative, be administered as a continuous infusion.

EXAMPLES

The compounds according to the invention as well as their chemical synthesis and the preparation of the starting materials are further illustrated in the following examples, which are not however intended to limit the invention.

Examples 2,3,4,6Tetra-O-acetyl-α-D-glucopyranosylbromide (1)

This compound was prepared in accordance with Kartha et al., and Jennings, H., J. Carbohydr. Chem. 9, 777–781 (1990).

2,3,4,6Tetra-O-acetyl-1,5-anhydro-D-glucitol (2)

To a solution of 44.8 g of compound 1 (109 mmol) in dry diethylether was added 55 ml bistributyltinoxide (109 mmol) and an equal quantity of polymethylhydrosiloxane (55 ml). The mixture was stirred at room temperature under nitrogen. TLC evaluation after 3 hours ($CH_2Cl_2$—MeOH 98:2) showed that all the 2,3,4,6-Tetra-O-acetyl-α-D-O-glucopyranosylbromide was converted into a more polar product. A solution of 15.80 g KF (2.5 eq, 272 mmol) in water was then added and the mixture stirred vigorously for 15 minutes. The $Bu_3SnF$ precipitate was filtered and washed with diethylether. After separation of the water the ether layer was dried above anhydrous $Na_2SO_4$ and evaporated dry. The compound of the title (2) (30.06 g, 90.5 mmol; 83% yield) was obtained after chromatographic purification [1) $CH_2Cl_2$ hexane 50:50; 2) $CH_2Cl_2$].

1,5 Anhydro-4,6-O-benzylidene-D-glucitol (3)

Removal of the protective groups of 2 was achieved by treating 30.06 g (90.5 mmol) of compound 2 with 400 ml 0.1 N NaOMe for 2 hours at room temperature. The mixture was neutralized with acetic acid and evaporated dry. After co-evaporation with toluene, 12.4 g (91 mmol) freshly dried $ZnCl_2$ and 46.5 ml (455 mmol) benzaldehyde were added and the suspension stirred vigorously for 1 to 2 days at room temperature.

The mixture was poured into cold water and extracted three times with ethyl acetate. The combined organic layer was dried on anhydrous $Na_2SO_4$. After filtration and removal of the solvent the excess benzaldehyde was partially removed under vacuum at 70° C. (oil pump). The solid residue was further purified by washing on a glass funnel with n-hexane followed by chromatographic purification [1) hexane —$HC_2Cl_2$ 1:1; 2) $CH_2Cl_2$; 3) $CH_2Cl_2$— MeOH 98:2]whereby 17.1 g (68 mmol) 75% yield of compound 3 was obtained.

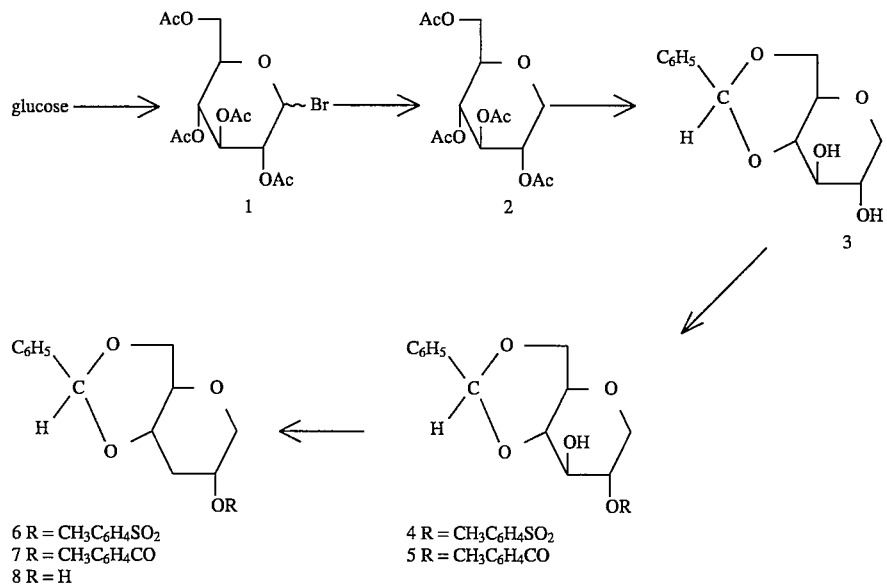

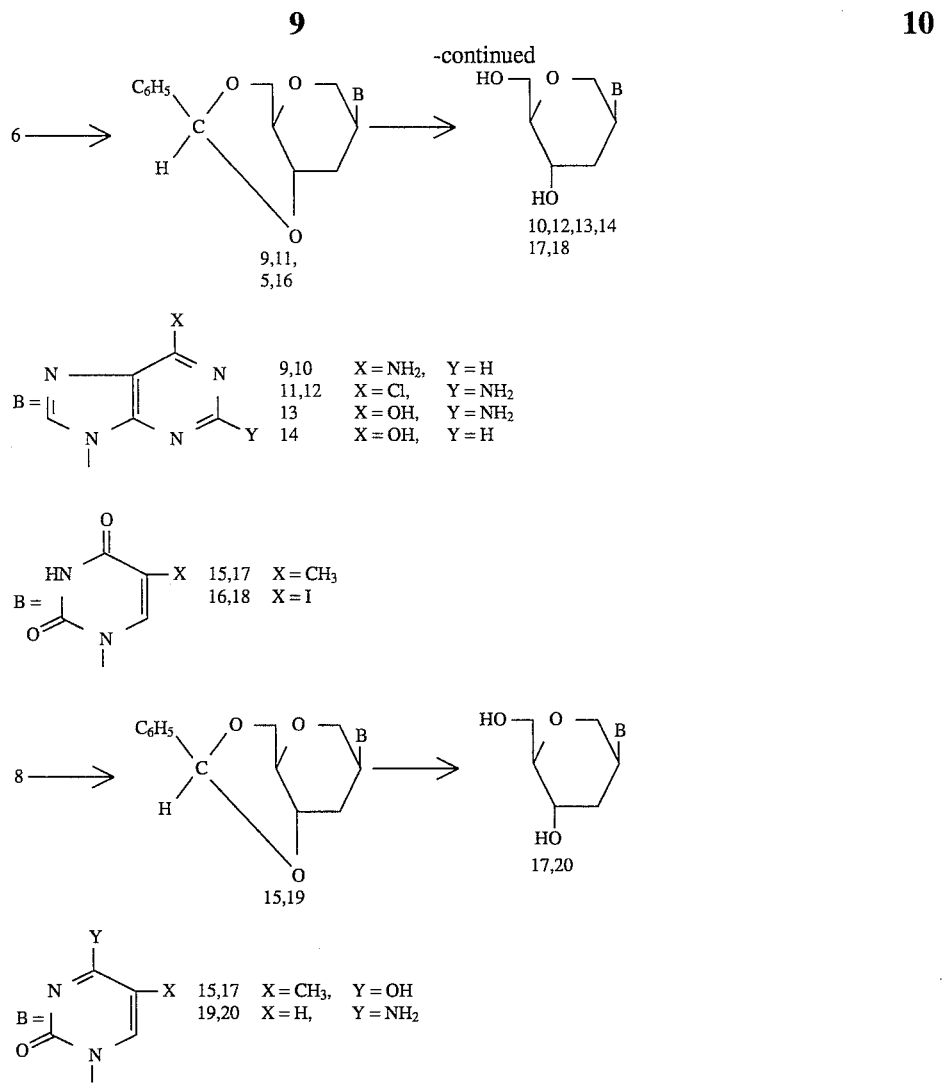

1,5-Anhydro-4,6-O-benzylidene-2-O-p-toluenesulphonyl-D-glucitol (4)

The glucitol derivative 3 (8.5 g, 33.67 mmol) and dibutyltinoxide (8.38 g, 367 mmol) were suspended in 250 ml benzene. The mixture was heated under reflux for 16 hours with azeotropic removal of water. After removal of the volatile substances the residue was dissolved in 150 ml anhydrous dioxane and 7.06 g (37.04 mmol) p-toluenesulphonylchloride was added. The mixture was heated to 50° C. for 6 hours, which resulted in a quantitative conversion to a less polar product. The mixture was concentrated, adsorbed on celite and purified by column chromatography ($CH_2Cl_2$ — hexane, 1:1; $CH_2Cl_2$;) to a yield of 11.22 g (27.6 mmol, 82%) of compound 4 as a white powder.
EIMS m/e: 406 ($M^+$)

400 MHz $^1H$ NMR (DMSO–$d_6$) δ 2.42 (s, 3H, $CH_3$), 3.35–3.42 (m, H-4, H-5), 3.49 (t, J=11Hz, 1H, H-1α), 3.61 (m, 1H, H-6), 3.67 (m, 1H, H-3), 3.87 (dd, J=5.5Hz and 11Hz, 1H, H-1β), 4.14–4.25 (m, 2H, H-2, H-6'), 5.05 (s, 1H, PhCH), 5.12 (d, J=5.5Hz, 1H, OH), 7.35–7.50 (m, 7H, arom-H), 7.85 (m, 2H, arom-H ) ppm.

90MHz $^{13}C$ NMR (DMSO-$d_6$) δ 21.0 ($CH_3$), 66.9, 67.6 (C-1, C-6), 70.7, 70.8 (C-3, C-5), 79.2, 80.4 (C-2, C-4), 100.7 (PhCH) +atom.

1,5-Anhydro-4,6-O-benzylidene-2-O-p-toluoyl-D-glucitol (5)

A suspension of the sugar derivative 3 (8.5 g, 33.67 mmol) and dibutyltinoxide (8.38 g, 33.67 mmol) in 250 ml benzene was boiled under reflux for 16 hours with azeotropic removal of water. The solution was concentrated and 150 ml dry dioxane was added. p-Toluoyl chloride (4.44 ml, 33.67 mmol) was added in droplets and the mixture was stirred for 5 hours at room temperature. The mixture was concentrated, adsorbed on celite and purified by column chromatography to a yield of 9.73 g (26.30 mmol, 78%) of compound 5 as a white powder.

1,5-Anhydro-4,6-O-benzylidene-3-deoxy-2-O-p-toluene-sul-phonyl-D-ribohexitol (6 )

A) 11.22 g (27.6 retool) of the tosylated sugar 4 and 23.60 g (193 mmol) of 4-dimethylaminopyridine (DMAP) were dissolved in 400 ml dry $CH_2Cl_2$. The reaction mixture was cooled to −40° C. and during vigorous stirring 2.53 ml thiophosgene (33.12 retool) was added. The mixture was brought to room temperature. After stirring for 1 hour 6.30 g (38.64 mmol) 2,4-dichlorophenol was added and stirring continued for 2 hours. The mixture was poured into 300 ml 1 M $KH_2PO_4$ and extracted twice with $CH_2Cl_2$. The organic layers were dried ($Na_2SO_4$), the volatile substances removed under vacuum and the residue purified by flash chromatography (hexane/$CH_2Cl_2$ 8:2 to $CH_{2Cl2}$)

B) the obtained thiocarbonyl compound was dissolved in 300 ml anhydrous toluene. After fast bubbling the solution for 10 minutes with $N_2$, 7.84 ml (29.15 mmol) tri-n-butyltinhydride and 325 mg (2 mmol) 2,2'-azobis(2-methyl-propionitrile) were added and the reaction mixture heated overnight at 80° C.

The mixture was evaporated and purified on silica gel with a yield of 6.90 g (17.67 mmol, 64%) of compound 6. CMIS ($NH_3$) m/e: 391 ($MH^+$)

1,5-Anhydro-4,6-O-benzylidene-3-deoxy-2-O-p-toluoyl-D-ribohexitol (7)

The reaction was performed as described for the synthesis of compound 6. Treating of 9.73 g (26.30 mmol) of the toluoylated hexitol 5 provided 6.79 g (19.73, 75%) of compound 7 after chromatographic purification.

1,5-Anhydro-4,6-O-benzylidene-3-deoxy-D-glucitol (8)

Removal of the toluoyl group of compound 7 was achieved by treating 6.79 g (19.73 mmol) thereof with 300 ml 0.1 M NaOMe for 4 hours at room temperature. After neutralizing and evaporation of the volatile substances the residue was purified by column chromatography ($CH_2Cl_2$— MeOH, 99:1) with a yield of 3.72 g (15.81 mmol, 80%) of the above compound.

1,5-Anhydro-4,6-O-benzylidene-2-(adenin-9-yl)-2,3-dideoxy-D-arabinohexitol (9)

A mixture of 1.35 g (10 mmol) adenine, 400 mg sodium hydride (60% dispersion, 10 mmol) and 529 mg (2 mmol) 18-crown-6 in 60 ml dry DMF was stirred for 1 hour at 80° C. After adding a solution of 1.95 g (5 mmol) of compound 6 in 30 ml anhydrous DMF the stirring was continued for 16 hours at 100° C. The reaction mixture was cooled and evaporated dry. the residue was dissolved in ethylacetate (100 ml) and the organic phase was washed with saturated $NaHCO_3$ solution (50 ml) and $H_2O$ (2×25 ml), dried and evaporated dry. The solid residue was purified by column chromatography ($CH_2Cl_2$— MeOH, 97:3) with a yield of 989 mg (2.8 mmol, 56% yield) of compound 9. A quantity of 190 mg (0.49 mmol, 9%) of the tosylate 6, which had not reacted, was recovered.

UV (MeOH): $\lambda_{max}$ 262 nm ($\epsilon$=11300)

MS (m/e): 353 ($M^+$)

$^1$H NMR ($CDCl_3$+DMSO-$d_6$) δ 2.0–2.6 (m, H-3', H-3"), 3.5–4.55 (m, 5H), 4.94 (m, 1H), 5.57 (s, PhCH), 7.10 (br, $NH_2$), 7.35 (m, 5H, Ph), 8.19 (s), 8.27 (s) (H-2, H-8)ppm.

$^{13}$C NMR ($CDCl_3$+ DMSO-$d_6$; internal ref. TMS) ) δ 32.6 (C-3'), 50.4 (C-2'), 68.2, 69.1 (C-1', C-6'), 73.6, 74.0 (C-4', C-5'), 101.2 (PhCH); 119.0 (C-5), 126.1,127.8, 128.6, 137.6 (Ph), 139.0 (C-8), 149.5 (C-4), 152.5 (C-2), 156.1 (C-6)ppm.

1,5-Anhydro-2-(adenin-9-yl) 2,3-dideoxy-D-arabinohexitol (10)

The benzylidene moiety of compound 9 was hydrolyzed by heating 989 mg (2.8 mmol) thereof in 100 ml 80% acetic acid at 80° C. for 3 hours. After evaporation and co-evaporation with toluene the residue was dissolved in water and washed with diethylether. The water layer was evaporated and the residue crystallized from MeOH-$Et_2O$ with a yield of 602 mg (2.27 mmol, 81% yield) of compound 10. mp: 237°–239° C.

UV (MeOH): $\lambda_{max}$ 261 nm ($\epsilon$=13500)

CIMS ($NH_3$) m/e: 266 ($MH^+$), 136 ($BH_2^+$)

$^1$H NMR (DMSO-$d_6$) δ 1.7–2.4 (m, H-3', H-3'), 3.2–4.3 (m, 6H), 4.53–5.02 (m, H-5', 4'-OH, 6'-OH), 7.25 (br s, NH2) 8.16 (s), 8.31 (s) (H-2, H-8)ppm. $^{13}$C NMR (DMSO-$d_6$) δ 36.0 (C–3'), 50.2 (C-2'), 60.6, 60.9 (C-4', C-6'), 68.1 (C-1'), 83.1 (C-5'), 118.2 (C-5), 139.7 (C-8), 149.4 (C-4), 152.5 (C-2), 156.1 (C-6)ppm. Anal.

1,5-Anhydro-4,6-O-benzylidene-2-(2-amino-6-chloropurin-9-yl)-2,3-dideoxy-D-arabinohexitol (11)

The 1,5-anhydrohexitol 6 (1.56 g, 4 mmol) and 848 mg (5 mmol) 2-amino-6-chloropurine were dissolved in 30 ml anhydrous DMF to which 830 mg (6 mmol) anhydrous potassium carbonate and 530 mg (2 mmol) 18-crown-6 were added. The mixture was stirred for 5 hours at 120° C. after which the volatile substances were removed under vacuum and the residue adsorbed on silica gel. Purifying produced 295 mg (0.76 mmol, 90%) of the compound 11.

$^1$H NMR ($CDCl_3$) δ 1.86–2.32 (m, H-3') 2.45–2.75 (m, H-3"), 3.5–3.9 (m, 3H), 4.07 (dd, J=2.6Hz and 13Hz, 1H), 4.34 (m, 2H), 4.77 (m, 1H), 5.30 (s, $NH_2$), 5.48 (s, PhCH), 7.2–7.5 (m, Ph), 8.27 (s, H-8)ppm.

$^{13}$C NMR ($CDCl_3$) δ 32.8 (C-3'), 50.8 (C-2'), 68.8, 69.2 (C-6', C-1'), 73.7, 74.6 (C-4', C-5'), 101.9 (PhCH), 125.9, 128.1, 128.9, 137.0, (Ph), 126.1 (C-5), 141.1 (C-8), 151.5 (C-6), 153.5 (C-4), 159.0 (C-2)ppm.

1,5-Anhydro-2-(2-amino-6-chloropurin-9-yl)-2,3-dideoxy-D-arabinohexitol (12)

The obtained compound 11 (295 mg, 0.76 mmol) was heated in 50 ml 80% acetic acid at 80° C. to complete hydrolysis of the benzylidene moiety. Evaporation and co-evaporation with toluene left behind an oil which was purified on silica gel ($CH_2Cl_2$— MeOH, 9:1). The product which precipitated after concentration of the eluate provided 145 mg (0.48 mmol, 63%) of compound 12.

UV (MeOH):$\lambda_{max}$ 224 (27000), 249 (6100), 310 (8000) nm.

$^1$H NMR (DMSO-$d_6$) δ 1.7–2.5 (H-3', H-3"), 3.94 (J=11Hz,), 4.18 (J=12Hz), 4.67 (t, J=5.5Hz, 6'-OH), 4.95 (d,J=5.2Hz, 4'-OH), 6.95 (s, $NH_2$), 8.30 (s, H-8)ppm.

$^{13}$C NMR (DMSO-$d_6$) δ 35.7 (C-3'), 50.3 (C-2'), 60.5, 60.7 (C-4', C-6'), 67.8 (C-1'), 83.0 (C-5'), 123.0 (C-5), 141.9 (C8), 149.5 (C-6), 154.0 (C-4), 159.8 (C-2)ppm.

1,5-Anhydro-2-(guanin-9-yl)-2,3-dideoxy-D-arabinohexitol (13)

A mixture of 145 mg (0.48 mmol) of compound 12 and 0.5 ml of a suspension of adenosine deaminase in 100 ml 0.05 M phosphate buffer, pH 7.5, was incubated for 4 hours at 30° C. The reaction mixture was concentrated to about 15 ml and the precipitate filtered off. Recrystallization from water provided 50 mg analytically pure compound 13. The filtrates were placed onto an XAD column (25×2 cm), which was eluted with water followed by MeOH-water (3:1). Evaporation gave an extra 70 mg of compound 13 as a white product to a total of 0.43 mmol (89%). mp >300° C.

UV (MeOH) $\lambda_{max}$ =253 nm ($\epsilon$=9100)

CIMS ($iC_4H_{10}$) m/e: 282 ($MH^+$)

$^1$H NMR (DMSO-$d_6$) δ 4.52 (br, 6'-OH), 4.9 (br, 4'-OH), 6.56 (br, $NH_2$), 7.87 (s, H-8)ppm.

$^{13}$C NMR (DMSO-$d_6$) δ 36.3 (C-3'), 50.2 (C-2'), 61.0, 61.2 (C-4'C-6'), 68 4 (C-1'), 83 2 (C-5'), 116 3 (C-5), 136.9 (C8), 151.5 (C-4), 154.1 (C-2) 157.9 (C-6)ppm.

Anal. ($C_{11}H_{15}N_5O_4$)

Calculated: C, 46.97; H, 5.38; N, 24.90

Found: C, 46.73; H, 5.40; N, 24.58

1,5-Anhydro-2,3-dideoxy-2-(5-iodouracil-1-yl)-D-arabinohexitol (18 )

A mixture of 2.60 g (10 mmol) of the sodium salt of 5iodouracil [prepared in accordance with Colla L. et al., Eur. J. Med. Chem., 17, 569 (1982)], 1.95 g (5 mmol) crude tosylate 6 and 528 mg (2 retool) 18-crown-6 in 80 mg dry DMF was stirred at 100° C. for 16 hours. The reaction mixture was cooled and evaporated dry. The residue was dissolved in 100 ml EtOAc and the organic layer was washed successively with saturated NaHCO$_3$ solution (50 ml) and water (3×50 ml), dried and evaporated dry. Column-chromatography (CH$_2$Cl$_2$— MeOH, 98:2) produced 958 mg (2.1 mmol, 42% yield) of compound 16 in the form of an oil and 371 mg (0.95 mmol) of the tosylate, which had not reacted, was recovered.

The obtained oil was heated in 100 ml 80% acetic acid at 80° C. to complete hydrolysis of the benzylidene moiety. The mixture was evaporated and co-evaporated with toluene and purified by column chromatography (CH$_2$Cl$_2$— MeOH, 90:10) affording 408 mg (1.11 mmol, 53% yield) of the compound 18 which crystallized out of MeOH.
mp 219°–220° C.
UV (MeOH): $\lambda_{max}$ 282 nm
CIMS (NH$_3$) m/e: 369 (MH$^+$)

$^1$H NMR (DMSO–d6) δ 1.53–2.42 (m, H-3, H-3 '), 2.8–4.2 (m, 6H), 4.53 (m, 1H), 8.47 (s, H-6)ppm.

$^{13}$C NMR (DMSO–d$_6$) δ 35.3 (C-3'), 51.4 (C-2'), 60.7, 61.1 (C-4', C-6'), 67.2, (C-1'), 68.3 (C-5), 82.7 (C-5'), 147.9 (C-6), 150.9 (C-2), 160.9 (C-4)ppm. Anal. (C$_{10}$H$_{13}$N$_2$O$_5$I×0.75 H$_2$O):
Calculated: C, 31.47; H, 3.83; N, 7.34
Found: C, 31.83; H, 4.14; N, 7.03

1,5-Anhydro-2,3-dideoxy2-(thymin-1-yl)-D-arabinohexitol (17)

The above compound was synthesized in the same manner from compound 6 but in very moderate yields. Better results are obtained when the alcohol 8 is used as starting point.

A suspension of 2.40 g (10.46 mmol) of N$^3$-benzoyl-thymine [prepared in accordance with Cruickshank et al., Tetrahedron Lett. 2.5., 681–684 (1984)], 1.23 g (5.23 mmol) of the alcohol 8 and 3.43 g (13.08 mmol) of triphenylphosphine in 100 ml anhydrous dioxane was treated with 2.06 ml (13.08 mmol) diethylazodicarboxylate (DEAD) in 15 ml anhydrous THF. The solution was stirred overnight at room temperature whereafter the volatile substances were removed under vacuum. The residue was resuspended in 100 ml methanol saturated with ammonia. Evaporation and co-evaporation with toluene left behind an oil which was purified on silica gel (CH$_2$Cl$_2$— MeOH, 98:2). This provided 3.5 g of crude compound 15 which also contained hydrazine dicarboxylate.

The crude compound 15 was resuspended in 50 ml 80% acetic acid and heated at 80° C. for 5 hours. After evaporation and co-evaporation with toluene the residue was dissolved in water and extracted with ether. The water layer was concentrated and purified on silica gel (CH2Cl$_2$— MeOH, 3:7). Crystallization out of MeOH-Et$_2$O provided 671 mg of the compound 17 as white crystals (2.62 mmol, 50% total yield).
mp 169–171° C.
UV (MeOH): $\lambda_{max}$ 272 nm (ε=9500)
CIMS (iC$_4$H$_{10}$) m/e: 257 (MH$^+$)

$^1$H NMR (DMSO–d$_6$) δ 1.77 (s, CH$_3$), 1.6–2.5 (m, H-3', H-3"), 3.05–3.30 (m, 1H), 3.4–4.1 (m, 5H), 4.52 (m, 1H), 4.65 (t, J=5.7Hz, 6'-OH), 4.89 (d, J=5Hz, 4'-OH) 7.88 (s, H-6), 11.25 (br, NH) ppm. $^{13}$C NMR (DMSO–d$_6$) δ 12.3 (CH3), 35.2 (C-3'), 50.1 (C-2'), 60.3, 60.8, (C-4', C-6'), 66.9 (C-1'), 82.4 (C-5'), 108.3 (C-5), 138.9 (C-6), 150.9 (C-2), 163.8 (C-4)ppm.

Anal. (C$_{11}$H$_{16}$N$_2$O$_5$×0.5 H$_2$O):
Calculated: C, 49.81; H, 6.46; N, 10.56
Found: C, 49.84; H, 6.52; N, 10.55

1,5-Anhydro-2-(cytosin-1-yl)-2,3-dideoxy-D-arabinohexitol (20)

A suspension of 2.15 g (10 mmol) of N$^3$-benzoylcytosine [prepared in accordance with Brown et al., J. Chem. Soc. 2384 (1956)], 1.18 g (5 mmol) of the alcohol 8 and 3.28 g (12.5 mmol) of triphenylphosphine in 100 ml anhydrous dioxane was treated with 1.97 ml (12.5 mmol) diethylazodicarboxylate in 20 ml anhydrous THF for 15 hours at room temperature. After removal of the volatile substances the residue was resuspended in 100 ml EtOAc and washed twice with 50 ml water.

The organic layer was dried on anhydrous Na$_2$SO$_4$, evaporated and adsorbed on silica gel. Purifying by column chromatography produced 800 mg (1.85 mmol, 37%) of the crude 1,5-anhydro-4,6-0-benzylidene-2,3-dideoxy-2-(N$^4$-benzoylcytosin-1-yl)-D-arabinohexitol.

The benzoyl group was removed by treatment with 70 ml NH$_3$/MeOH for 5 hours at room temperature. Evaporation left an oil which was purified on silica gel (CH$_2$Cl$_2$— MeOH, 98:2) to a yield of 400 mg of the debenzoylated derivative as an oil.

The obtained oil was treated with 50 ml 80% acetic acid at 80° C. for 5 hours. After evaporation and co-evaporation with toluene the residue was dissolved in water and washed with diethylether. The water layer was evaporated and the precipitate crystallized out of MeOH-Et$_2$O with a yield of 234 mg of the compound 20 (0.97 mmol, 80%).
UV (MeOH): $\lambda_{max}$ 276 nm (8200)
CIMS (iC$_4$H$_{10}$) m/e: 242 (MH$^+$)

$^1$H NMR (DMSO–d$_6$) δ 1.47–1.87 (m, H-3), 1.91–2.28 (m, H-3'), 2.95–3.30 (m, 1H, H-2), 3.35–4.10 (m, 5H), 4.52 (m, 2H, 6'-OH +H-5'), 4.85 (d, J=4.8Hz, 4'-OH), 5.66 (d, J=7.5Hz, H-5), 6.99 (s, NH$_2$), 7.97 (d, J=7.5Hz, H-6)ppm.

$^{13}$C NMR (DMSO–d6) δ 35.7 (C-3'), 51.5 (C-2'), 61.0, 61.2 (C-4', C-6'), 67.9 (C-1'), 82.9 (C-5'), 93.7 (C-5), 144.3 (C-6), 156.3 (C-2), 165.7 (C-4)ppm.

Anal. (C$_{10}$H$_{15}$N$_3$O$_4$)
Calculated: C, 49.79; H, 6.27; N, 17.42
Found: C, 49.85; H, 6.27; N, 17.20

1,5-Anhydro-2,3-dideoxy-2-(5-ethyluracil-1-yl)-D-arabinohexitol (24)

A suspension of 736 mg (3 mmol) of N$^3$-benzoyl-5-ethyluracil prepared in analogy with the preparation of N$^3$-benzoyl thymine [Cruickshank et al., Tetrahedron Lett. 25, 681–684 (1984)], 471 mg (2 mmol) of the alcohol]and 1,5 g (4 mmol) of triphenylphosphine in 50 mL of anhydrous THF was treated with 630 μL (4 mmol) of diethylazodicarboxylate (DEAD) in 10 mL of anhydrous THF.

The solution was stirred overnight at room temperature after which the volatiles were removed in vacuo. The residue containing 21 was taken up in 50 mL of methanol saturated with ammonia. Evaporation and coevaporation with toluene left an oil which was purified on silica gel (CH$_2$Cl$_2$— MeOH, 98:2). This yielded 2.3 g of crude 1,5-anhydro-4,6-O-benzylidene-2-(5-ethyluracil-1-yl)-D-arabinohexitol 22 which also contained hydrazine dicarboxylate and triphenylphosphinoxide. The crude compound was taken up in 50 mL 80% acetic acid and heated at 80° C. for 5 h. After evaporation and coevaporation with toluene, the residue was dissolved in water and extracted with CH$_2$Cl$_2$. The water layer was concentrated and purified by preparative thin layer chromatography (CH$_2$Cl$_2$— MeOH, 85:15). Crystallisation from MeOH—Et$_2$O) afforded 240 mg of 23 as white crystals (0.89 mmol, 44% overall yield).

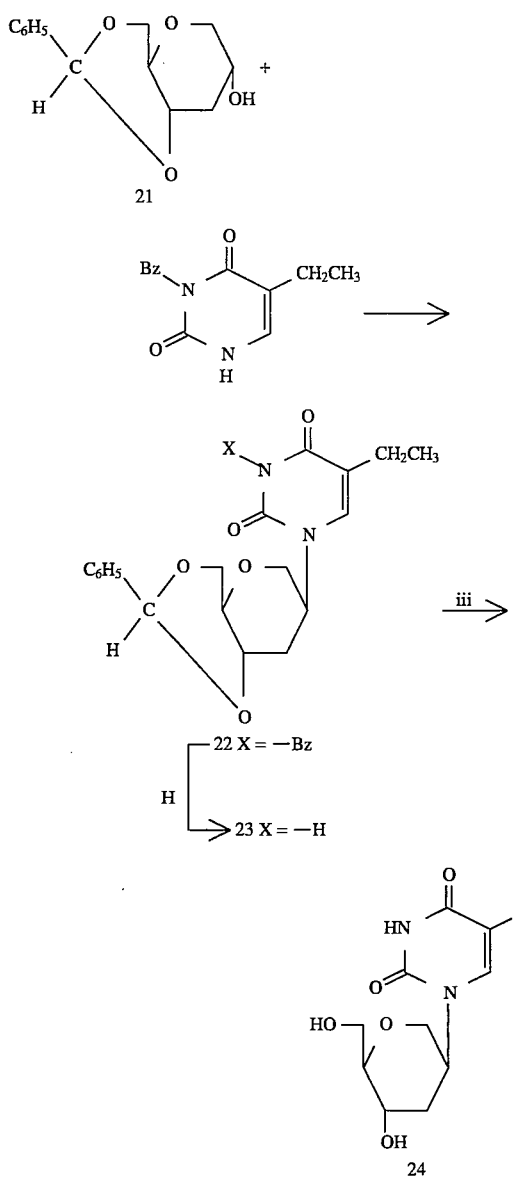

(i) Ph3P, DEAD, THF; (ii) NH$_3$/CH$_3$OH; (iii) 80% HOAc.
UV (MeOH) λ max 270 nm (ε=10.600)
EIMS: m/e 270 (M$^+$), 141 (BH$^+_2$)
200 MHz $^1$HNMR (DMSO–d$_6$) 0.91–1.12 (t, J =7.4 Hz, 3H, CH$_3$), 1.59–1.84 (m, 1H, H-3'ax), 1.98–2.30 (m, 3H, CH$_2$, H-3'$_{eq}$), 3.05–3.22 (m, 1H, H-5 '), 3.25–3.88 and 3.95–4.16 (m, H-4', H-6', H-6", H-1', H-1"), 4.51 (s, 1H, H-2'), 4.78 (s, 1H, D$_2$O exchangeable, 6'-OH), 4.98 (s, 1H, D$_2$O exchangeable, 4'OH), 7.85 (s, 1H, H-6), 11.21 (br s, 1H, NH)ppm. 200 MHz $^{13}$C NMR (DMSO–d$_6$) δ 13.2 (CH$_3$), 19.7 (CH$_2$), 35.4 (C-3'), 50.2 (C-2'), 60.4, 60.7 (C-4', C-6'), 67.1 (C-1'), 82.5 (C-5'), 114.1 (C-5), 138.4 (C-6), 150.8 (C-2), 163.8 (C-4) ppm.
Anal. (C$_{12}$H$_{18}$N$_2$O$_5$·1H$_2$O) C, H, N.

ANTI-VIRAL TESTS

The anti-viral activity of the compounds according to the invention in respect of the herpes virus and related viruses is illustrated by the following tests. In these tests the effect was determined of the 1,5-anhydrohexitol nucleoside analogues according to the invention on the growth and yield of the virus in cell cultures.

The compounds used are described in the examples together with a number of well known anti-herpes agents from tile prior art, that is, BVDU or E-5-(2-bromovinyl)-2'-deoxyuridine, Ribavirin or 1-ribofuranosyl-3-carbamoyl-1,2,4-triazol, (S)DHPA or (S)-9-(2,3-dihydroxypropyl)-adenine and C-c$^3$ Ado or carbocyl 3-deaza adenosine.

The compounds were tested against herpes simplex virus type 1 (HSV-1), herpes simplex virus 2 (HSV-2) and vaccinia virus (VV). These viruses were cultured in human embryonal skin muscle (E$_6$SM) fibroblast cell cultures.

The tests were based on the inhibition of virus-induced cytopathogenesis in cell cultures. A standard procedure is described by De Clercq et al., J. Infect. Dis. 141, 463 (1980) which is incorporated herein by way of reference.

Test 1

In this test the inhibiting activity of the test compounds against viruses was measured in E$_6$SM cell cultures. The cells were cultured to confluence in microtitre (R) plates and then inoculated with 100 CCID$_{50}$ virus, wherein a CCID$_{50}$ of the virus corresponds with the virus dose required to infect 50% of the cell cultures. After a virus adsorption period of an hour remaining virus was removed and the cell cultures incubated in the presence of different concentrations of the test compounds (varying from 0.001 µg/ml to 400 µg/ml). For each virus cell system the ED$_{50}$ was determined, that is, the concentration of the compound required to suppress the cytopathic effect of the virus by 50%. This cytopathic effect was noted as soon as it reached completion in the non-treated, virus-infected cell cultures. In addition the minimum cytotoxic concentration of each compound was measured. The results are shown in table I.

Test 2

Further, the inhibiting effect of the test compounds on virus multiplication in E$_6$SM cell cultures was measured making use of herpes simplex viruses missing a specific thymidine kinase. Three different strains were used: TK$^-$Cheng, TK$^-$Field and a clinically isolated strain VMW/837. The results are shown in table II.

TABLE I

Cytotoxicity and anti-viral activity of nucleoside analogues in human embryonal skin muscle (E$_6$SM) fibroblast cultures.

| Compound | Minimum cytotoxic concentration[a] (µg/ml) | Minimum inhibiting concentration[b] ED$_{50}$ (µg/ml) | | |
|---|---|---|---|---|
| | | HSV-1 (KOS) | HSV-2 (G) | VV |
| 10 | >400 | 7 | 7 | 20 |
| 13 | >400 | 0.2 | 0.1 | 2 |
| 18 | >400 | 0.07 | 0.07 | 150 |
| 17 | >400 | 40 | 150 | >200 |
| 20 | >400 | 0.7 | 0.04 | 0.7 |
| IDU | >400 | 0.2 | 0.2 | 0.2 |
| BVDU | >400 | 0.004 | 10 | 0.2 |
| (S)-DHPA | >400 | 70 | 300 | 20 |
| Ribavirin | >400 | 70 | 70 | 70 |
| C-c$^3$Ado | >400 | >400 | 40 | 0.7 |

[a]Required to cause a microscopically detectable change in the normal cell morphology
[b]Required to reduce the virus-induced cytopathogenesis by 50%

TABLE II

Cytotoxicity and anti-viral activity of nucleoside analogues in human embryonal skin muscle ($E_6SM$) fibroblast cultures.

| Compound | Minimum cytotoxic concentration[a] (µg/ml) | Minimum inhibiting concentration[b] $ED_{50}$ (µg/ml) | | |
|---|---|---|---|---|
| | | HSV-1 TK⁻Cheng C 158/77 | HSV-2 TK⁻Field C 137/101 | VV VMW/837 #3 |
| 10 | >400 | 150 | 70 | 20 |
| 13 | >400 | 20 | 20 | 2 |
| 18 | >400 | >200 | >200 | 1 |
| 17 | >400 | >200 | >200 | >200 |
| 20 | >400 | 2 | 2 | 2 |
| IDU | >400 | 10 | 10 | 7 |
| BVDU | >400 | 10 | 10 | 4 |
| (S)-DHPA | >400 | 400 | >400 | >400 |
| Ribavirin | >400 | >400 | >400 | >400 |
| C-c³Ado | >400 | 70 | >400 | >400 |

[a]Required to cause a microscopically detectable change in normal cell morphology
[b]Required to reduce virus-induced cytopathogenesis by 50%

Test 3

The cytotoxicity and antiviral activity of compound 24 were tested in various cell cultures. Table III shows the results for $E_6SM$ cells.

TABLE III

Cytotoxicity and antiviral activity of compound 24 in $E_6SM$ cell cultures

| Compound | Minimum cytotoxic concentration[a] (µg/ml) | Minimum inhibitory concentration[b] (µg/ml) | | | | | |
|---|---|---|---|---|---|---|---|
| | | Herpes simplex virus-1 (KOS) | Herpes simplex virus-2 (G) | Vaccinia virus | Vesicular stomatitis virus | Herpes simplex virus-1 TK⁻ B2006 | Herpes simplex virus-1 TK⁻ VMW1837 |
| 23 | >200 | <0.04 | 0.2 | >200 | >200 | >200 | >200 |
| BVDU | ≧200 | 0.004 | >200 | 0.7 | >200 | 1 | 70 |
| (S)-DHPA | ≧200 | >200 | >200 | 20 | 20 | 100 | >200 |
| Ribavirin | >400 | 200 | >400 | 70 | 20 | 100 | >400 |
| C-c³Ado | ≧200 | >200 | >200 | 0.2 | 0.2 | 70 | >200 |

[a]Required to cause a microscopically detectable alteration of normal cell morphology.
[b]Required to reduce virus-induced cytopathogenicity by 50%.

We claim:

1. 1,5-Anhydrohexitol nucleoside analogues represented by the general formula I:

$$R^1O-\underset{X}{\underset{|}{\bigcirc}}-B \quad (I)$$

wherein the hexitol has the D-configuration and the carbon atom on which the base moiety and the X substituent stand both have the (S)-configuration and further wherein:

B is a heterocyclic ring selected from the group consisting of pyrimidine and purine bases, and X represents hydrogen, azido, F, Cl, Br, I, amino, $-NHR^2$, $-N(R^2)_2$, $-OR^2$, $-SR^2$ or CN;

wherein $R^1$ and $R^2$ are the same or different and are selected from the group consisting of hydrogen, substituted or unsubstituted $C_1-C_{20}$ alkyl, substituted or unsubstituted $C_1-C_{20}$ alkenyl, aroyl, $C_1-C_{20}$ alkanoyl, and phosphoryl and pharmaceutical salts thereof.

2. 1,5-Anhydrohexitol nucleoside analogues of claim 1, wherein X represents hydroxyl.

3. 1,5-Anhydrohexitol nucleoside analogues of claim 1, wherein the heterocyclic ring is represented by the formula III:

$$\text{(III)}$$

wherein:

X represents OH, $NH_2$, or NHQ, wherein: Q represents OH or $C_{1-5}$ alkyl;

Y represents H, F, Cl, Br, I, $C_{1-5}$ alkyl, haloethyl or CH=CH—R, wherein R represents hydrogen, halogen or $C_{1-5}$ alkyl and wherein haloethyl contains 1–4 F, Cl or Br atoms.

4. 1,5-Anhydrohexitol nucleoside analogues of claim 1, wherein the heterocyclic ring is selected from the group consisting of substituted adenine, adenine, guanine, 2,6-diaminopurine, hypoxanthine and xanthine.

5. 1,5-Anhydrohexitol nucleoside analogues of claim 1, wherein the heterocyclic ring is selected from the group consisting of aza-, deaza-, deoxy- and deamino- analogues of the pyrimidine and purine bases.

6. 1,5-Anhydro-2,3-dideoxy-2-(5-iodo-uracil-1-yl)-D-arabinohexitol.

7. 1,5-Anhydro-2,3-dideoxy-2-(5-ethyl-uracil-1-yl)-D-arabinohexitol.

8. Pharmaceutical composition comprising as the active ingredient a 1,5-anhydrohexitol nucleoside analogue of formula I, $$R^1O-\underset{X}{\underset{|}{\bigcirc}}-B \quad (I)$$

wherein the hexitol has the D-configuration and the carbon atom on which the base moiety and the X substituent stand both have the (S)-configuration and further wherein:

B is a heterocyclic ring selected from the group consisting of pyrimidine and purine bases, and X represents hydrogen, azido, F, Cl, Br, I, amino, —NHR$^2$, —N(R$^2$)$_2$, —OR$^2$, —SR$^2$ or CN;

wherein R$^1$ and R$^2$ are the same or different and are selected from the group consisting of hydrogen, substituted or unsubstituted C$_1$–C$_{20}$ alkyl, substituted or unsubstituted C$_1$–C$_{20}$ alkenyl, aroyl, C$_1$–C$_{20}$ alkanoyl and phosphoryl and a pharmaceutically acceptable carrier.

9. The pharmaceutical composition of claim 8, wherein the active ingredient is present in a concentration between about 0.1 and 100% by weight.

10. The pharmaceutical composition of claim 8, in the form of a powder, suspension, solution, spray, emulsion, salve or cream.

11. The analogues as claimed in claim 1, wherein the aroyl is selected from the group consisting of benzoyl, substituted benzoyl and naphthoyl.

12. The pharmaceutical composition of claim 8, wherein the aroyl is selected from the group consisting of benzoyl, substituted benzoyl and naphthoyl.

13. 1,5-Anhydrohexitol nucleoside analogues represented by the general formula II:

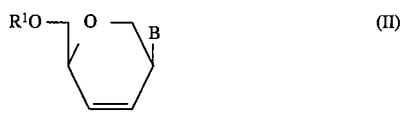 (II)

wherein the hexitol has the D-configuration and the carbon atom on which the base moiety stands has the (S)-configuration and further wherein:

B is a heterocyclic ring selected from the group consisting of pyrimidine and purine bases, and R$^1$ is selected from the group consisting of hydrogen, substituted or unsubstituted C$_1$–C$_{20}$ alkyl, substituted or unsubstituted C$_1$–C$_{20}$ alkenyl, aroyl, substituted or unsubstituted C$_1$–C$_{20}$ alkanoyl and phosphoryl and pharmaceutical salts thereof.

14. Pharmaceutical composition comprising as an active ingredient a 1,5-anhydrohexitol nucleoside analogue of formula II:

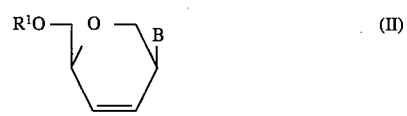 (II)

wherein the hexitol has the D-configuration and carbon atom on which the base moiety stands has the (S)-configuration and further wherein:

B is a heterocyclic ring selected from the group consisting of pyrimidine and purine bases, and R$^1$ is selected from the group consisting of hydrogen, substituted or unsubstituted C$_1$–C$_{20}$ alkyl, substituted or unsubstituted C$_1$–C$_{20}$ alkenyl, aroyl, substituted or unsubstituted C$_1$–C$_{20}$ alkanoyl and phosphoryl and a pharmaceutically acceptable carrier.

* * * * *